(12) United States Patent
Durack

(10) Patent No.: US 9,470,617 B2
(45) Date of Patent: Oct. 18, 2016

(54) FLOW CYTOMETRY APPARATUS

(75) Inventor: Gary P. Durack, Urbana, IL (US)

(73) Assignees: Sony Corporation, Tokyo (JP); Sony Corporation of America, New York, NY (US)

( * ) Notice: Subject to any disclaimer, the term of this patent is extended or adjusted under 35 U.S.C. 154(b) by 488 days.

(21) Appl. No.: 13/082,011

(22) Filed: Apr. 7, 2011

(65) Prior Publication Data

US 2012/0081709 A1    Apr. 5, 2012

Related U.S. Application Data

(60) Provisional application No. 61/321,684, filed on Apr. 7, 2010.

(51) Int. Cl.
*G01N 33/00*    (2006.01)
*E03B 1/00*    (2006.01)
*G01F 13/00*    (2006.01)
*G01N 15/14*    (2006.01)

(52) U.S. Cl.
CPC ......... *G01N 15/14* (2013.01); *G01N 2015/149* (2013.01)

(58) Field of Classification Search
CPC ........... G01N 2015/149; G01N 33/48; G01N 15/147; G01N 33/5005; G01N 2015/1006; G01N 15/14; G01N 15/1404; G01N 15/1427; G01N 15/1429; G01N 15/1459; G01N 2015/1075; G01N 2015/1415; G01N 2015/1438; G01N 2015/1477; G01N 15/06; G01N 15/1484; G01N 21/55; G01N 21/63; C12Q 1/02
USPC ..... 422/73, 930; 137/1, 2, 3, 4, 5, 8, 10, 13, 137/38, 39, 44, 803, 804, 806, 807, 833, 137/834, 837, 87.01, 93, 100, 109, 110, 137/111, 112, 113, 114
See application file for complete search history.

(56) References Cited

U.S. PATENT DOCUMENTS 5,180,065 A * 1/1993 Touge et al. .................. 209/577
7,842,244 B2 11/2010 Skylar et al.
2005/0112541 A1* 5/2005 Durack ................ C12N 5/0612
435/2
2011/0020855 A1* 1/2011 Shinoda et al. ................ 435/29

* cited by examiner

*Primary Examiner* — Dean Kwak
(74) *Attorney, Agent, or Firm* — Ice Miller LLP

(57) ABSTRACT

A high speed fluid switch is used to separate desired particles from a source stream containing particles, such as cells. A droplet generator creates and regulates a stream of droplets, which intersects with a source stream containing the particles to be sorted. The stream of droplets can be regulated such that portions of the source stream containing desired particles are deflected into a collection vessel, or such that portions of the source stream containing desired particles are permitted to pass uninterrupted. The high speed fluid switch may be implemented on a microfluidic chip.

14 Claims, 9 Drawing Sheets

FLOW CYTOMETRY APPARATUS

CROSS-REFERENCE TO RELATED APPLICATIONS

This application claims the benefit of the filing date of U.S. Provisional Application No. 61/321,684, filed Apr. 7, 2010, which is hereby incorporated by reference in its entirety.

TECHNICAL FIELD OF THE INVENTION

The present disclosure generally relates to fluid handling and, more particularly, to a high speed fluid switch.

BACKGROUND OF THE INVENTION

High speed cell sorting has been an important research technology for many years. Examples of the many applications include isolation of rare populations of immune system cells for AIDS research, isolation of genetically atypical cells for cancer research, isolation of specific chromosomes for genetic studies, and isolation of various species of microorganisms for environmental studies. However, its high cost and mechanical complexity have limited its use in clinical applications.

Recently, two areas of interest are moving cell sorting towards patient care applications. First is the move away from chemical pharmaceutical development to biopharmaceuticals. The majority of new cancer therapies are developed using biotechnology. These include a class of antibody-based cancer therapeutics. Cell sorters can play a vital role in the identification, development, purification and ultimately the production of these products. Related to this is a move toward the use of cell replacement therapy for patient care. Much of the interest in stem cells revolves around a new area of medicine often referred to as regenerative therapy or regenerative medicine. These therapies may often require that large numbers of relatively rare cells be isolated from patient tissue. For example, adult stem cells may be isolated from bone marrow and ultimately used as part of a re-infusion back into the patient from whom they were removed.

High speed cell sorters have typically utilized an electrostatic droplet technology similar to that used in early ink jet printers. This method is very efficient, allowing as many as 90,000 cells to be sorted per second from a single stream. This method is not, however, particularly biosafe. Aerosols generated in the droplet formation process can carry biohazardous material. Even though "biosafe" droplet cell sorters mounted in a biosafety cabinet are commercially available, even this type of system does not lend itself to the sterility and operator protection required for routine sorting of patient samples in a clinical environment.

Microfluidics technologies offer great promise for providing cell sorting capability on a "chip." Many microfluidic systems have been demonstrated that can successfully sort cells. They have the advantage of being completely self-contained, easy to sterilize, and can be manufactured in sufficient quantities to be a disposable part. These technologies have not been widely adopted largely due to cost considerations related to the maximum throughput achievable on such a device. The fastest of these devices operate at rates of 1000-2000 cells per second, nearly ten times slower than a droplet cell sorting system. One of the speed limitations of microfluidic devices is the ability to sort desirable cells from the remaining cells quickly. All of the cells move together in a stream of fluid, and the desired cells must be routed into a collection vessel while the remaining cells are routed into a waste vessel. The present disclosure relates to a high speed means for achieving such sorting, and can be implemented in a microfluidic device or in a more traditional droplet cell sorter.

SUMMARY OF THE INVENTION

In a first embodiment of the invention, a flow cytometry apparatus comprises a source flow containing particles that are to be sorted, and a droplet generator positioned such that the droplets it generates intersect with the source flow.

In a second embodiment of the invention, a micro-flow device, comprises a source channel, a deflection channel, a waste channel, and at least one collection reservoir. The source channel is adapted to receive a source flow containing particles that are to be sorted. The deflection channel is adapted to receive a stream of droplets from a droplet generator. The deflection channel intersects the source channel, such that the stream of droplets and the source flow intersect. The waste channel is positioned to receive droplets and portions of the source flow that have collided. At least one collection reservoir is positioned to receive portions of the source flow that do not collide with droplets from the droplet generator.

In a third embodiment of the invention, a flow cytometry apparatus, comprises a micro-flow device, having a source channel, a deflection channel, a waste channel, and at least one collection vessel. The source channel is adapted to receive a source flow containing particles that are to be sorted. The deflection channel is adapted to receive a stream of droplets from a droplet generator, which intersects the source channel, such that the stream of droplets and the source flow intersect. The waste channel is positioned to receive droplets and portions of the source flow that have collided. The at least one collection vessel, positioned to receive portions of the source flow that do not collide with droplets from the droplet generator. A beam of electromagnetic radiation, such as a laser beam, that intersects the source flow at a point upstream from the point at which the stream of droplets intersect the source flow, in conjunction with appropriate optics and detectors as is known in the art, identifies desired particles. Portions of the source flow containing identified desired particles are deposited in the collection vessel, and other portions of the source flow are removed from the micro-flow device through the waste channel.

In a fourth embodiment of the invention, particles are sorted by a method comprising the steps of providing a set of criteria for distinguishing desired particles from undesired particles; providing a source flow containing particles that are to be sorted; generating a stream of droplets that intersects the source flow; identifying desired particles within the source flow according to the criteria; and regulating the stream of droplets to separate portions of the source flow containing the identified desired particles from the other particles in the source flow.

In a fifth embodiment of the invention, a method of flow cytometry includes the step of deflecting portions of the source flow by collision with droplets moving in a different direction.

DETAILED DESCRIPTION OF VARIOUS EMBODIMENTS

Figure 1:
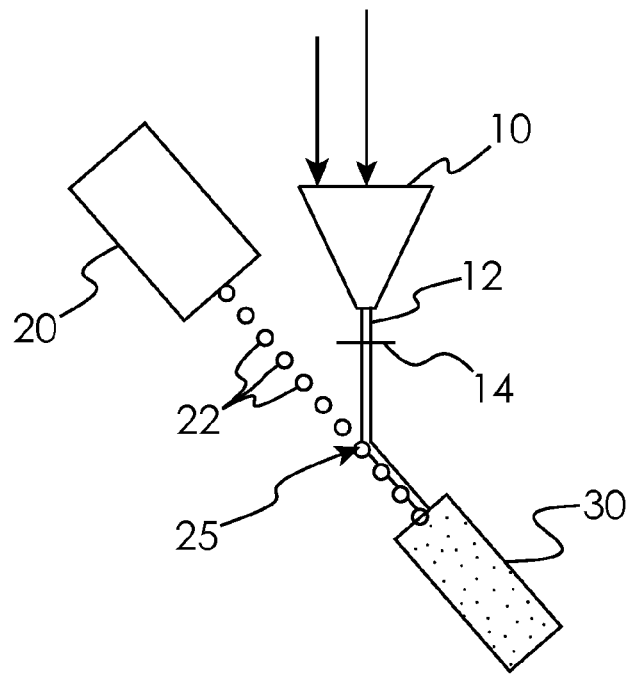
FIG. 1 is a schematic diagram of an embodiment of the invention in which the source flow is laminar, shown in a case in which the entire source flow is deflected into a waste receptacle.

For the purposes of promoting an understanding of the principles of the invention, reference will now be made to embodiments illustrated in the drawings, and specific language will be used to describe them. It will nevertheless be understood that no limitation of the scope of the invention is thereby intended. Alterations and modifications in the illustrated device, and further applications of the principles of the invention as illustrated therein, as would normally occur to one skilled in the art to which the invention relates, are contemplated.

The embodiments of the present invention described below solve some major problems that currently exist in the field of cell sorting. It will be appreciated by those skilled in the art that a number of efforts have been made in recent years to improve the rate and quality of sorting provided by flow cytometry. A number of these are discussed, for example, in U.S. Pat. No. 7,842,244, to Skylar, et al. So far, however, none of these approaches has permitted sorting from a single stream at frequencies on the order of tens of kilohertz. Furthermore, it remains very difficult to implement cell sorting in a completely closed environment.

The various embodiments disclosed herein may be implemented in various physical formats, such as an injection molded microfluidic chip, microchannel device, or micro-injection molded structure, to name just a few non-limiting examples, (collectively referred to herein as "micro-flow devices"). The embodiments described below can be implemented economically in a disposable micro-flow device to provide a completely closed and sterile path for cell sorting. A high speed fluid switch is provided, which can operate at many tens of kilohertz. Together, the benefits of the various embodiments can help make existing treatments, such as stem cell treatments using CD34-antigen cells sorted from blood marrow, more economical, as well as making feasible a range of new treatments.

One of the advantages of the various embodiments that can provide these benefits is the freedom from constraints on the properties of the jet formation for the stream of cells being sorted (i.e. the stream that contains the cells). Traditional droplet-based cell sorting requires that the stream that contains the cells be broken into droplets (because the sorting is accomplished by placing a charge on the individual droplets that contain a cell of interest, and then deflecting the droplets by passing them though a static electric field). Since ideally there is only a single cell in a droplet, the frequency of droplet formation establishes an upper rate limit for sorting. The maximum frequency of droplet formation for a given nozzle diameter and fluid density is governed by the pressure of the fluid inside the nozzle. On traditional cell sorters the fluid containing the cells must be placed under pressure (typically 1 0psi-90 psi) and then jetted through a small, round orifice, which produces significant shear force on the cell. Many cells cannot survive the shear forces at the higher pressures, and therefore can only be sorted at nozzle pressures below 30 psi).

In the various embodiments disclosed herein, however, there is no need to create these high shear forces, because the pressure on the fluid that contains the cells can be kept low. This is because it is not necessary to break this stream into droplets. The interference stream does not contain cells and can be operated at very high pressures and high droplet frequencies. Because the shear force constraint has been removed, the interference stream can be operated a much higher pressure than the stream that contains cells. This higher pressure enables higher droplet frequency than previously possible. The higher frequency allows the cell stream to be segmented into smaller segments which enables higher throughput or sorting rate.

Similarly, this advantage of the various embodiments can improve the purity of the sorting, and permits sorting of a wider range of cell types. Traditional cell sorting requires that the time from measurement to pinch-off of the droplets made in the stream of cells be held constant to a high precision. This is necessary to allow the measurement system to predict which segment of the measured stream will make up a particular drop. If this time interval varies, then the sort efficiency and purity suffers. The presence of cells in the stream causes instability in droplet formation or pinch-off, and this limits the efficiency of traditional cell-sorters. Large cells, like macrophage or neurons, create substantial instability and cannot be easily sorted using traditional cell sorting. In the various embodiments disclosed herein, however, the stream of cells can support any size or length of cell, and the segment sorted can be adjusted in real time by leaving gaps equal to multiple droplets. The interfering droplets are particle free, and therefore there is no particle or cell related instability in droplet formation. Since they have no dependency on the sample, nor the media that contains the sample, all properties of the interfering stream (velocity, position, temperature, density, droplet pinch-off point) are easy to hold constant to a high precision. The interfering stream may be composed of the same liquid that forms the stream of sample cells, or it may be formed from a different liquid. If two different liquids are used, they may be non-miscible to prevent mixing, or they may be miscible to promote mixing. If mixing is promoted, then the deflected stream can be a very accurate mix of two very small and tightly controlled volumes.

On traditional cell sorters, the droplets are generated synchronously but the sample cells arrive randomly. This means that sample cells are not necessarily centered in the droplet volume, thus reducing the probability of actually sorting the cell. With the collision approach disclosed herein, it is possible to adjust the stream segment chosen so that the cell is always at the center of the segment, thus improving recovery and sort efficiency.

Another advantage of the various embodiments is that there is no need to introduce charges to the stream of cells. This charging can cause undesirable effects on the cells, and it can involve components of the system in unwanted electrolysis. Droplet charging requires that electrical current must flow through the fluid that contains the cells. This current can have an undesirable effect on cell function or viability. The various embodiments eliminate the need for high voltage deflection plates and the charging apparatus. In addition to removing undesirable potential side effects, it can also reduce cost and improve the reliability of the system.

Yet another advantage of the various embodiments is greatly improved ease in performing the cell sorting in an enclosed environment provided by the micro-flow device. It is very difficult to implement traditional cell sorting in a completely closed environment. The ability to perform high-speed cell sorting in an enclosed environment is a significant advantage for sorting biohazardous material or pathogenic material. The various embodiments described below, however, can easily be implemented within such a micro-flow device.

Figure 2:
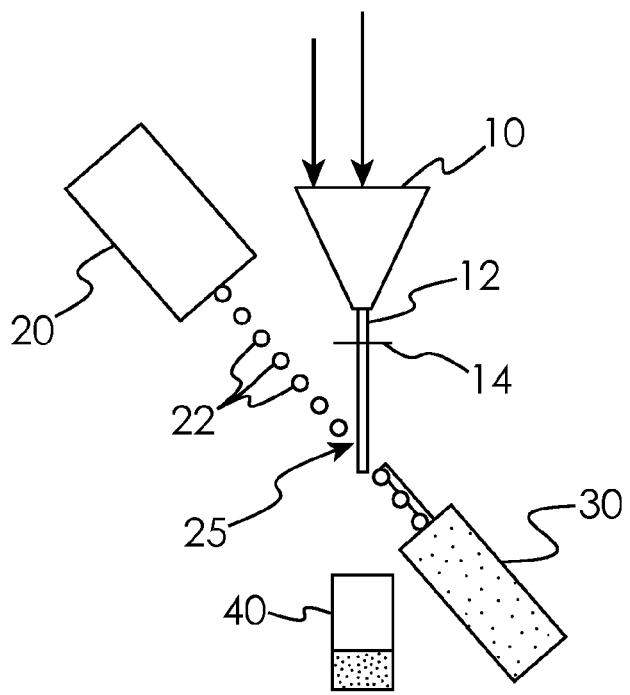
FIG. 2 is a schematic diagram of an embodiment of the invention in which the source flow is laminar, shown in a case in which a segment of the source flow is permitted to pass uninterrupted into the collection vessel.
Figure 3:
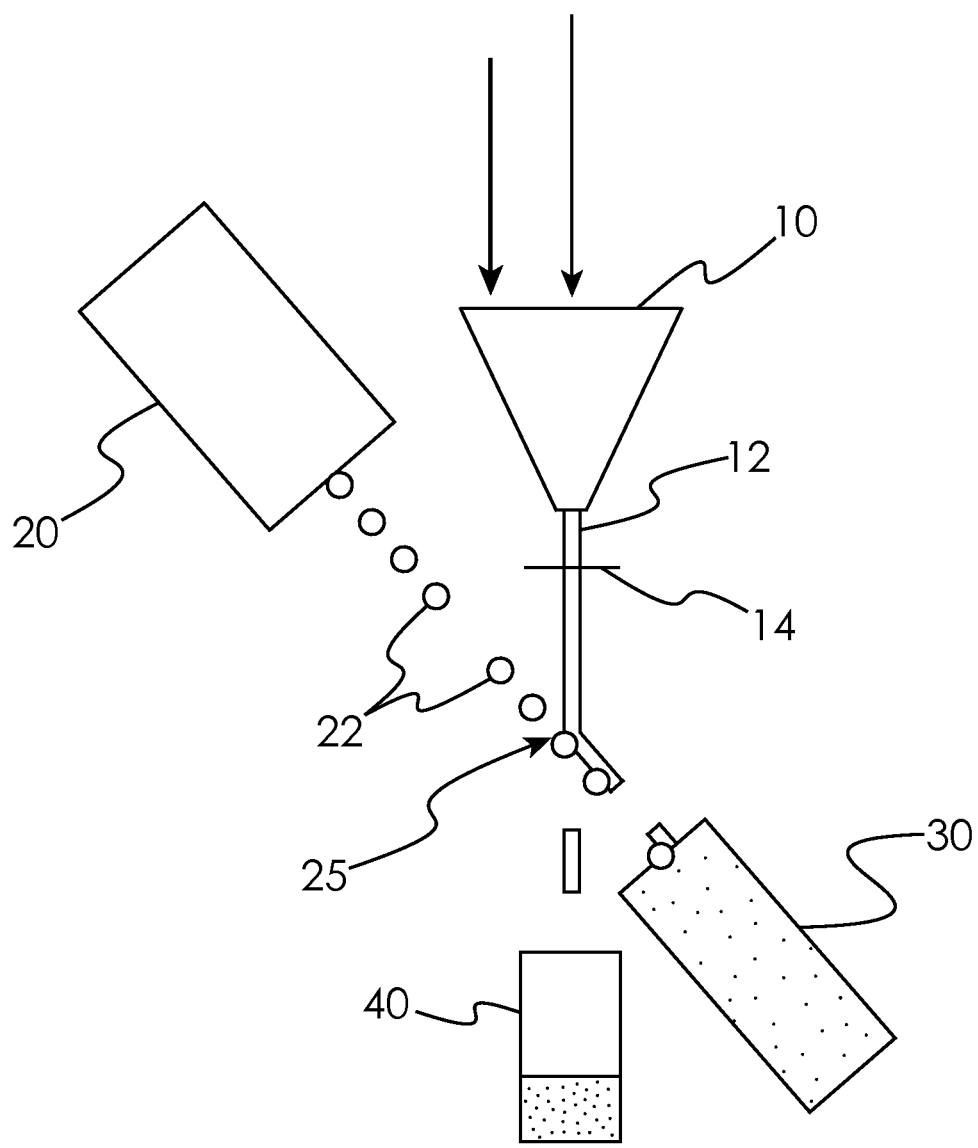
FIG. 3 is a schematic diagram of an embodiment of the invention in which the source flow is laminar, at a later point in time in the case shown in FIG. 2.

FIGS. 1-3 show a first embodiment of the present invention. The sample source 10 contains the cells (or other material) to be sorted, and feeds them into a laminar flow 12. Using a co-axial flow system and hydrodynamic focusing in the nozzle (as is typical in flow cytometry) the cells are aligned in single file at the center of the flowing stream. In some embodiments, the cells flow within a laminar stream of air (or other gas) or within a vacuum. In other words, the channel in which the jetted stream of cells flows is void of fluid surrounding the jetted stream. A droplet generator 20 is positioned to propel droplets 22 that intersect the laminar flow 12 at a point 25 downstream from the detection point 14 of the detection optics path, such as a detection laser beam (or other source of electromagnetic radiation used in the detection system). A waste receptacle 30 is positioned to capture the combined fluid of the droplets 22 and the laminar flow 12 resulting from the intersection at point 25. FIG. 1 illustrates a case in which no cells for collection are detected, and the entire laminar flow 12 is being diverted to the waste receptacle 30. FIG. 2 illustrates a case in which some desired cells have been detected in the laminar flow 12. As described further hereinbelow, the droplet generator 20 creates gaps in the stream of droplets 22. As shown in FIG. 3, this results in segments of the laminar flow 12 to pass uninterrupted into the collection vessel 40. By synchronizing the time delay between the flow between the detection point 14 and the interception point 25 with the time delay between the nozzle (or other aperture) of the droplet generator 20 and the interception point 25, the portions of the laminar flow 12 containing desired cells can be permitted to pass uninterrupted into the collection vessel 40.

Figure 4:
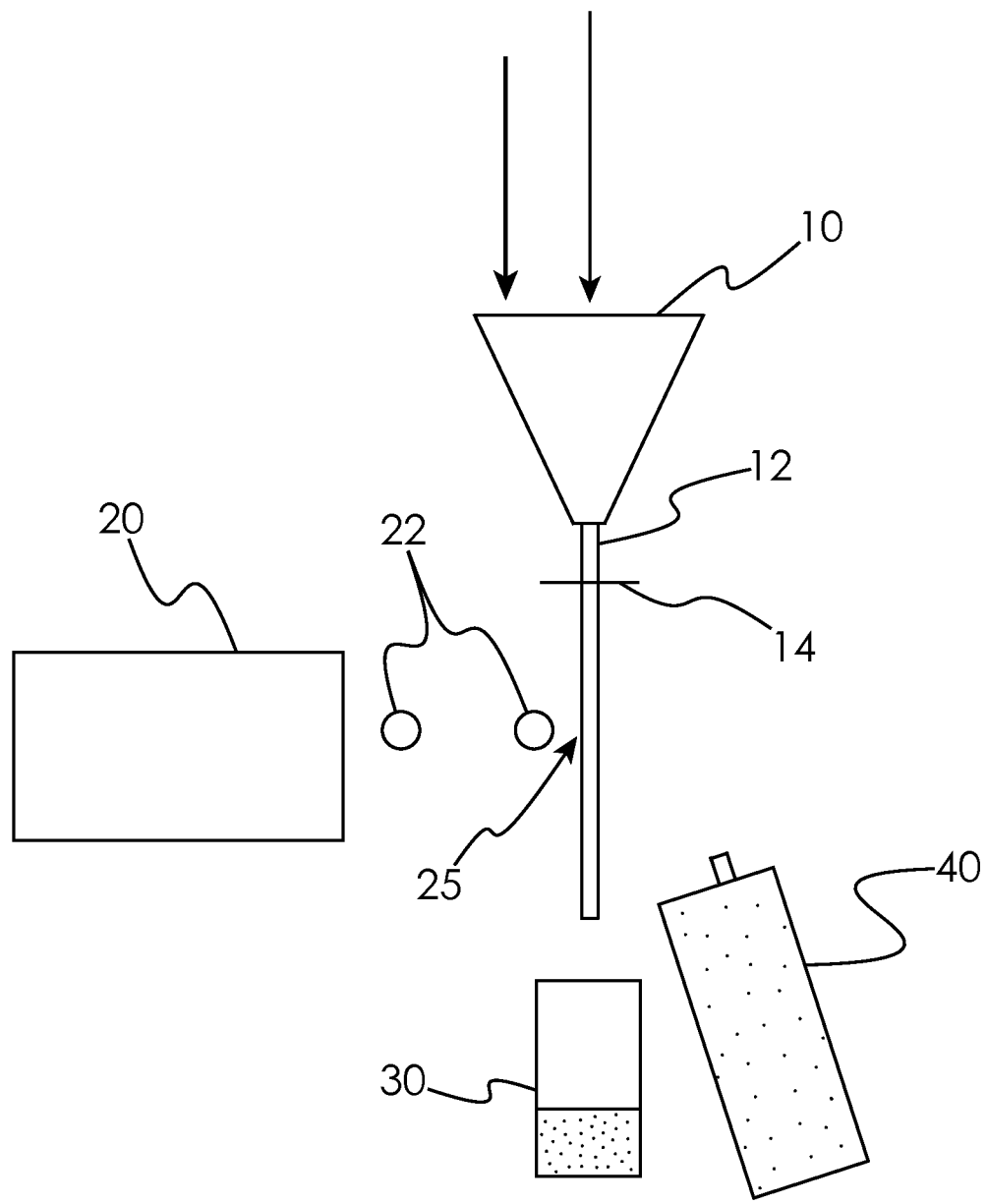
FIG. 4 is a schematic diagram of an embodiment of the invention in which the source flow is laminar, and in which the collection vessel is positioned to capture desired particles that are deflected by collision with droplets from the droplet generator.
Figure 5:
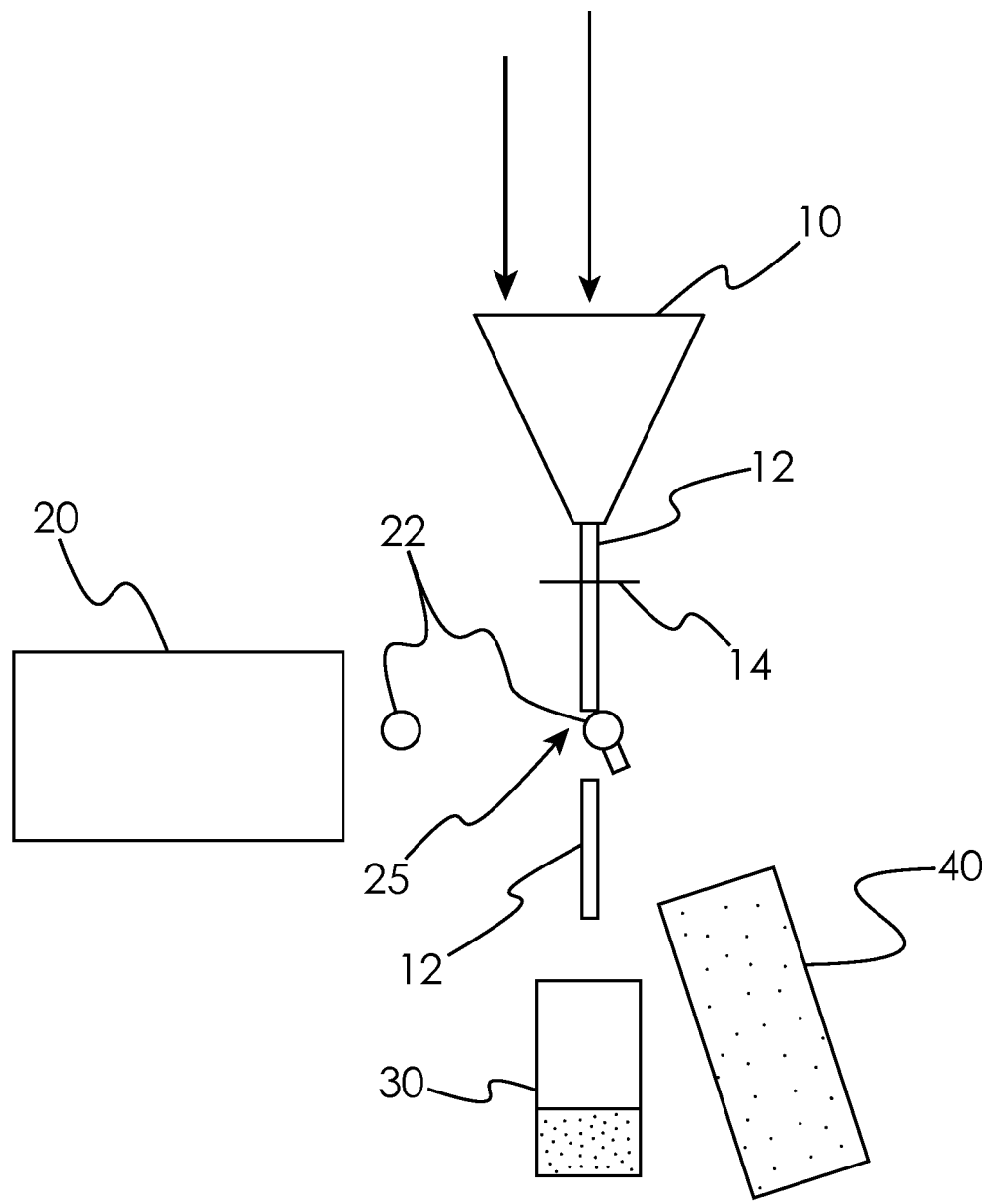
FIG. 5 is a schematic diagram of the embodiment shown in FIG. 4, shown at a point in time in which a droplet is colliding with the source flow.
Figure 6:
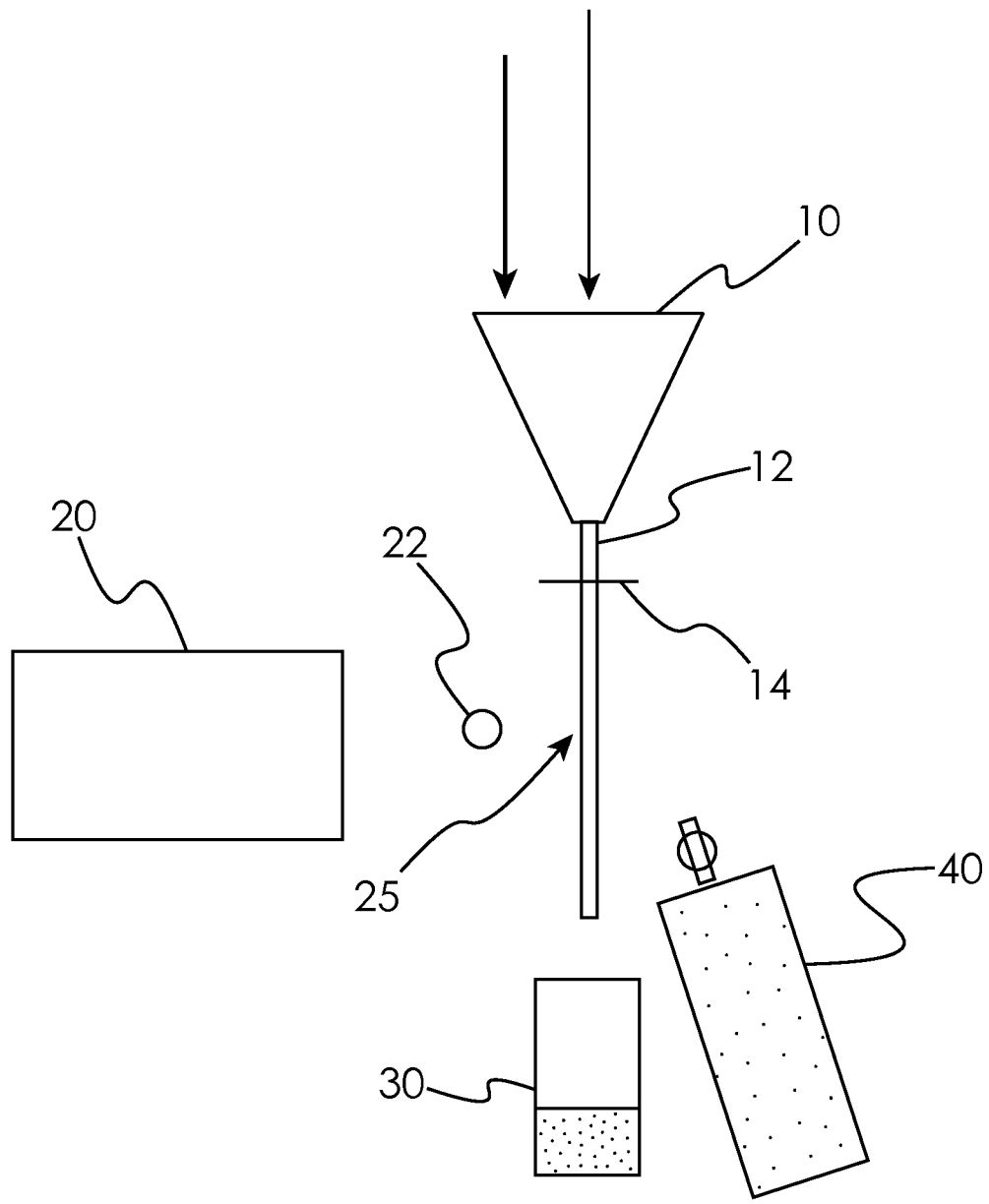
FIG. 6 is a schematic diagram of the embodiment shown in FIG. 5, shown at a later point in time.

FIGS. 4-6 show a second embodiment of the present invention. Again, a sample source 10 feeds cells (or other material) into a laminar flow 12, and, again, a droplet generator 20 fires a stream of droplets 22 that intersects the laminar flow 12 at a point 25 downstream from its point of intersection with the detection laser 14. In this case, however, the portions of the laminar flow 12 that do not contain desired cells are permitted to pass uninterrupted into the waste receptacle 30. A collection vessel 40 is positioned to capture the fluid resulting from the intersection of droplets 22 with the laminar flow 12.

Figure 7:
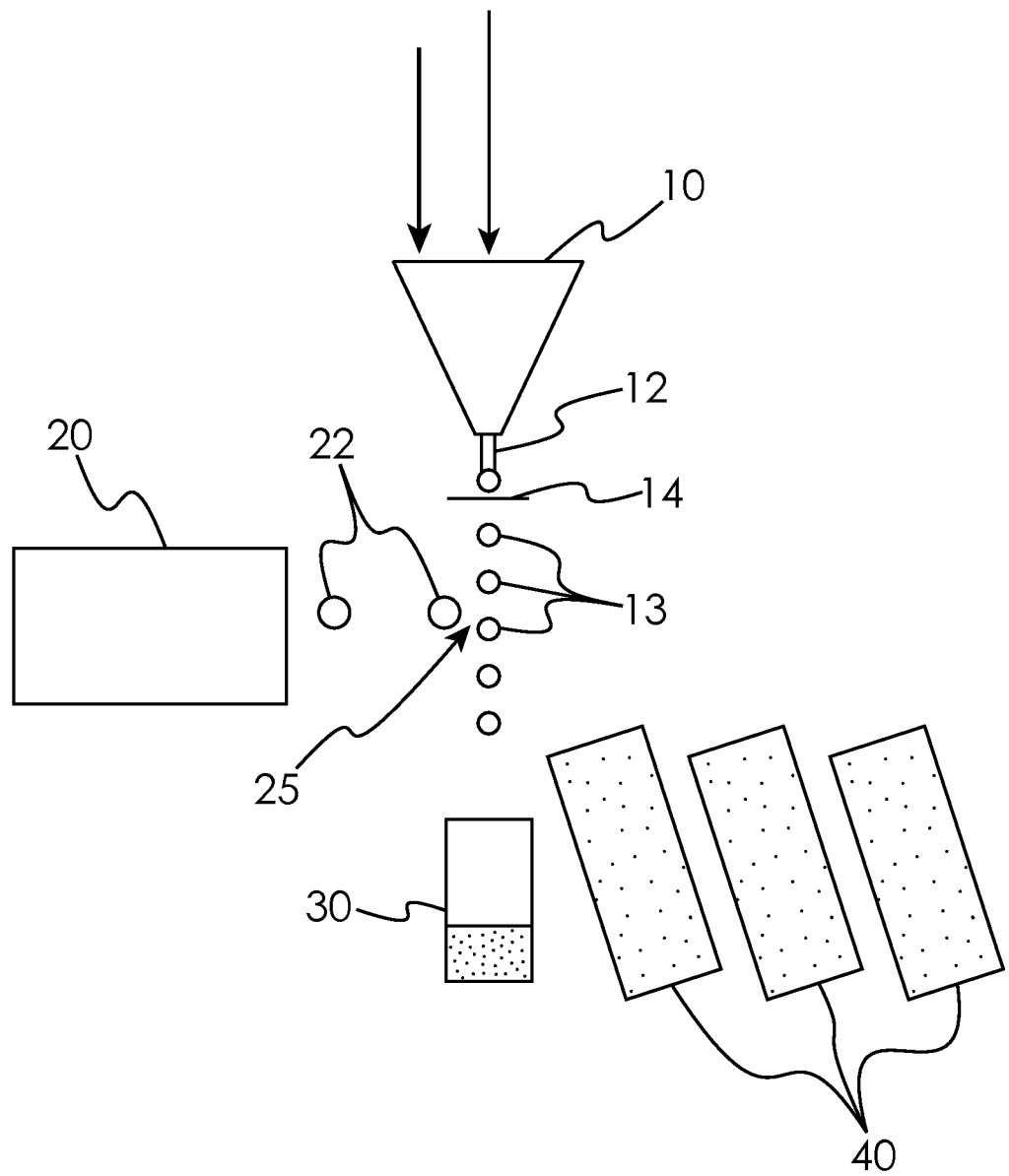
FIG. 7 is a schematic diagram of an embodiment of the invention in which the source flow is separated into droplets, and having several collection vessels.
Figure 8:
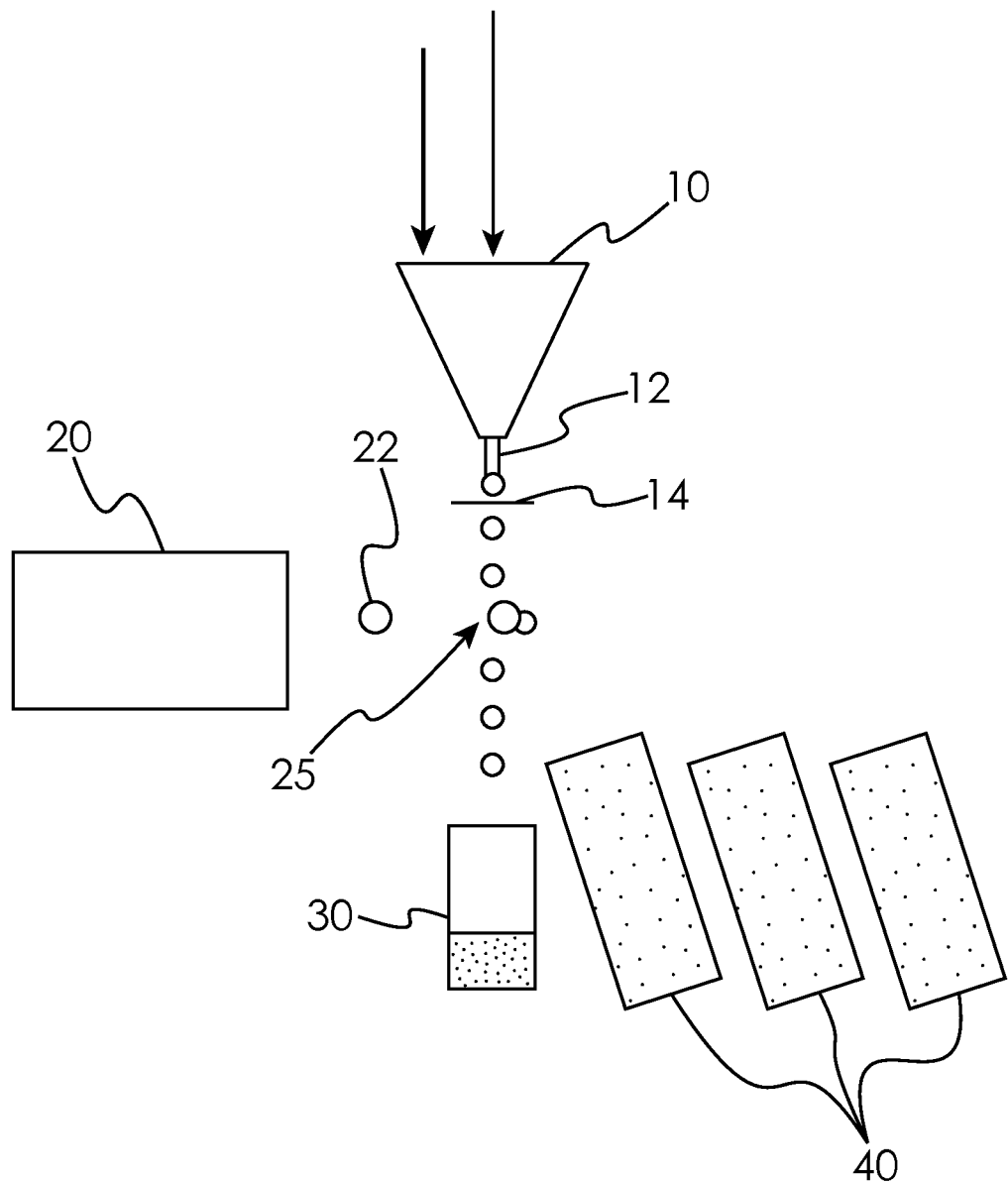
FIG. 8 is a schematic diagram of the embodiment of the invention shown in FIG. 7, at a point in time when a droplet from the collision droplet generator is colliding with a droplet in the source flow.
Figure 9:
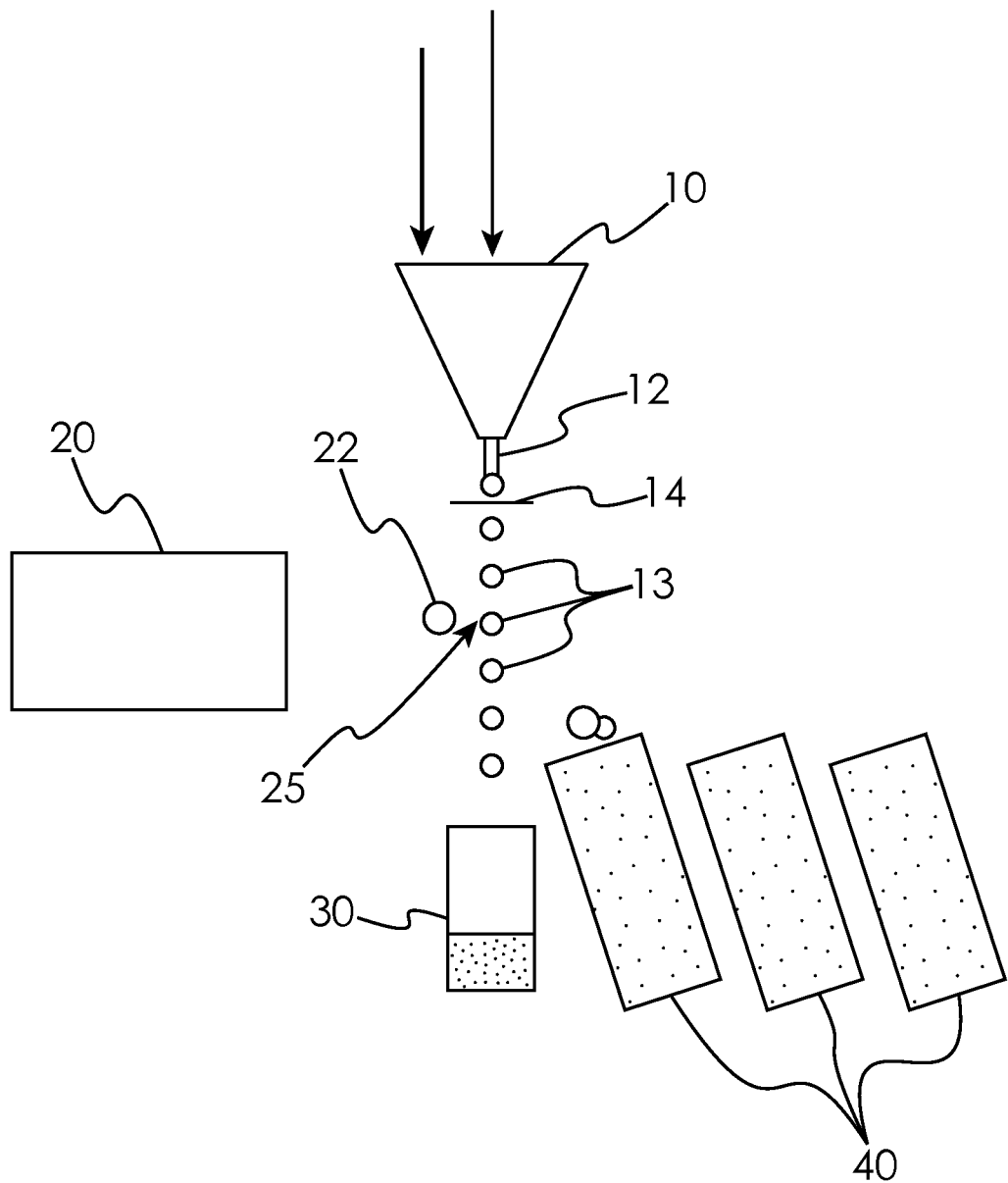
FIG. 9 is a schematic diagram of the embodiment shown in FIG. 8, shown at a later point in time.

FIGS. 7-9 show a third embodiment of the present invention. In this embodiment droplets are formed in both the stream of cells and the collision stream. Thus, the laminar flow 12 is replaced with a stream of sample droplets 13. As in the second embodiment, described above, fluid from the cell source 10 without desired cells is permitted to pass uninterrupted into the waste receptacle 30, while desired cells are deflected into a collection vessel 40 with collision droplets 22.

The droplet generator 20 can be a traditional flow cytometry nozzle. In this case, the sorting frequency can be improved because the fluid in the interference stream can be optimized for droplet formation, both through the absence of particles in the fluid, as well as by choice of fluid properties. In other embodiments, the droplet generator 20 is similar to those used for ink jet printing. In certain embodiments, the droplet generator 20 is a piezoelectric printing head.

Such a device can generate droplets at a frequency of several kilohertz. At high pressures this can be tens of kilohertz. It is also possible to make the interference stream any diameter, including a diameter that is larger than the sample cell stream. It is also possible to select or design the fluid used in the interference stream to adjust properties such as viscosity, specific gravity, and surface tension. The interference stream is adjusted to that it intersects the stream of cells. Upon intersection, the two streams combine and then proceed on a new trajectory that is determined by the sum of the momentum vectors. The angle of incidence of the two streams is selected so that the spacing between adjacent droplets is small enough to prevent any of the stream of cells from traveling straight through along the initial trajectory. It will be appreciated that the angle can be adjusted to select for a specific spacing between collisions of successive interference droplets 22 with the stream of cells (either the laminar flow 12 or the steam of droplets 13).

Any of the embodiments disclosed herein can be modified by adding additional collection vessels 40, as illustrated in FIGS. 7-9. In this way, more than one kind of desired cell (or other material) can be simultaneously sorted. This can be accomplished by including multiple droplet generators 20 to create streams of collision droplets 22 that intersect the stream of cells at multiple locations and/or with varying angles of incidence. In this way, different types of desired cells can be deflected into different collection vessels 40 by targeting each type of desired cell with a different one of the droplet generators 20. Alternatively, a droplet generator 20 may vary the mass or velocity of the interference droplets 22 to deflect cells into different collection vessels 40. By controlling the momentum of the interfering droplet 22, the distance that the laminar flow stream segment is moved may be controlled. It will be appreciated from the present disclosure that the droplet generator does not need to be synchronous. A piezoelectric device (or other appropriate droplet generator) may be programmed to produce varying volume droplets in an asynchronous manner. When an appropriate control system detects a portion of the stream of cells that need to be deflected, the control system can activate the piezoelectric device with the proper timing to causes the collision droplets to intersect the stream of cells at the appropriate location, wherein the collision droplets have the proper momentum to deflect the stream into the desired collection vessel 40.

Figure 10:
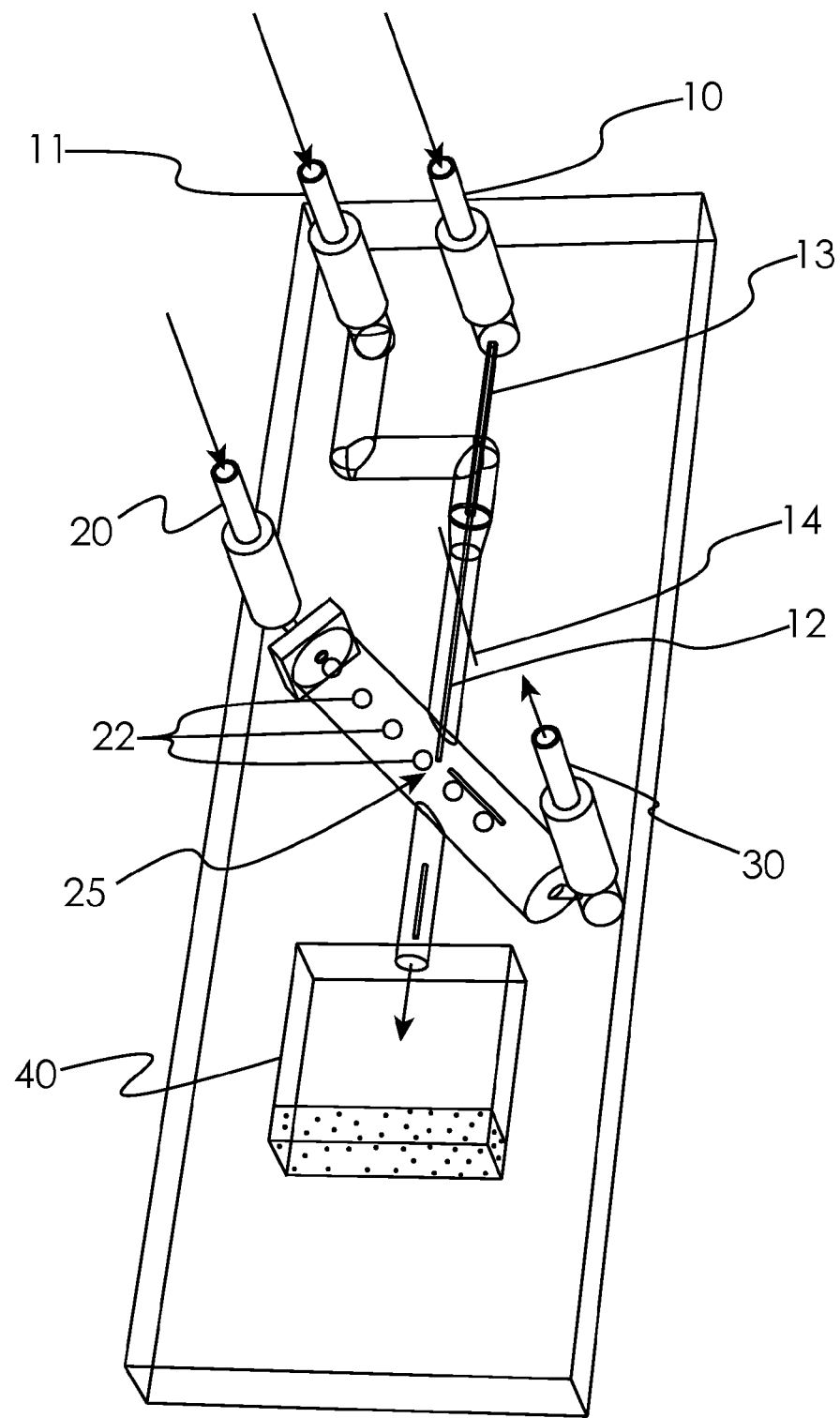
FIG. 10 is a diagram of a micro-flow device implementing a high speed fluid switch.

The various embodiments described above can be implemented in a micro-flow application. FIG. 10 shows a perspective schematic view of a micro-flow chip that embodies the present invention. Sample cells are supplied at 10 while a sheath fluid (such as air or another gas) is supplied at 11.

A laminar source flow 12 is created by injecting the sample cells from source 10 through a narrow passage 13 into the center of the sheath fluid. In other embodiments, the sample cells are jetted in a vacuum. A HEPA filtered vacuum source or pump may be used in order to provide biocontainment of the sample. Therefore, there is no fluid between the sides of the jetting stream and the walls of the microfluidic channel as there would be in a traditional microfluidic device. This gap is filled with air, vacuum, or other gas. Since the fluid containing the sample does not contact the walls of the micro-flow device, there is no parabolic flow as in a traditional device. It will be appreciated that this jetting stream segment can be incorporated into a traditional microfluidic device between traditional microfluidic channels that move liquid around the device.

Desired particles are permitted to pass into the collection reservoir 40 at the bottom of the chip (as depicted in FIG. 10); portions of the laminar flow 12 without desired particles are deflected into the waste passage 30. As shown in FIG. 10, the ports into which the sample, sheath and collision fluids are introduced, and through which the waste fluid is vented, are positioned on the face of the chip. However, these ports may alternatively be positioned at the edges of the chip or on the rear of the chip. It will be appreciated from the above disclosure that the collected sample may be made to exit the chip while the waste fluid is retained onboard the chip, or that the collected sample and the waste fluid may both be made to exit the chip.

The fluid for the droplets 22 is introduced at port 20 and a droplet generator onboard the device produces the droplets 22 when activated by a controller (not shown). The controller includes a non-transient computer readable medium programmed to control the droplet generator. The droplets 22 are jetted from the droplet generator along the desired trajectory to intersect the sample stream at point 25. The droplet generator (or its output nozzle) may be molded into the device substrate, or it may be a separate unit that is attached to the device substrate in such a manner as to allow the droplets 22 to be jetted toward the point of intersection 25.

An advantage of the presently disclosed embodiments is that the cell stream can be kept very small in diameter so that the dilution factor is low (i.e., the concentration is high). If the channel in which the sample flows were filled, rather than jetting the sample stream through a sheath of gas or vacuum, a much greater volume of sample would be required or the channel would have to be very small in cross section. A small cross section requires very high pressure to move the sample through it, resulting in cell damage (as discussed above) and mechanical failure from action of the pressure on the system components. This presently disclosed embodiments allow both low pressure on the sample and the ability to work with very small volumes of sample.

The presently disclosed embodiments are advantageous for many other uses besides cell sorting. The presently disclosed embodiments can be used to automatically meter very small calibrated volumes of a fluid or particle suspension for industrial applications like pharmaceutical development, to name just one non-limiting example.

In the various embodiments described above, identification of the particles is performed by a laser and associated optics and detection devices, as is known in the art. It will be appreciated, however, that other types of detection devices are known in the art of cytometry, and any suitable device may be used. The particular method of identifying features of the particles is immaterial.

For the purpose of this document, the terms "particle" and "cell" refer to anything that may be detected using a flow cytometry apparatus. The term "source" refers to any source of particles that are supplied to a flow cytometry apparatus. The term "flow cytometry" refers to a process in which particles are physically sorted from one another according to some predetermined criteria, and to distinguish from "cytometry," in which particles are merely observed in order to quantify different types of particles within a sample.

While the invention has been illustrated and described in detail in the drawings and foregoing description, the description is meant to be illustrative, and not restrictive in character. Only the preferred embodiments, and certain alternative embodiments deemed useful for further illuminating the preferred embodiments, have been shown and described. All changes and modifications that come within the spirit of the invention are desired to be protected.

What is claimed is:

1. A flow cytometry apparatus, comprising:
   a source flow containing particles that are to be sorted, wherein the source flow extends along a source flow axis;
   an interference stream fluid;
   a droplet generator receiving the interference stream fluid to generate interference droplets from the interference stream fluid, wherein the interference droplets extend along an interference droplet axis disposed at a non-zero angle with respect to the source flow axis such that the interference droplets the droplet generator generates intersect with the source flow downstream from the droplet generator;
   at least one collection vessel comprising a first collection vessel and a second collection vessel; and
   a controller having a non-transient computer readable medium programmed to control the droplet generator to generate first interference droplets having a first momentum to sort desired particles in the source flow into the first collection vessel through interference with the source flow, the non-transient computer readable medium further programmed to control the droplet generator to generate second interference droplets having a second momentum that is different than the first momentum to sort desired particles in the source flow into the second collection vessel through interference with the source flow.

2. The flow cytometry apparatus of claim 1, further comprising:
   a detection optics path that intersects the source flow at a point upstream from the point at which the interference droplets intersect the source flow; and
   at least one waste receptacle,
   wherein at least one portion of said source flow containing desired particles is identified by the detection optics and is deposited in the at least one collection vessel, and other portions of the source flow are deposited in the at least one waste receptacle.

3. The flow cytometry apparatus of claim 2, wherein the source flow identified as containing desired particles passes into the at least one collection vessel without collision with the interference droplets from the droplet generator.

4. The flow cytometry apparatus of claim 2, wherein the source flow and collection vessel are contained within a micro-flow device.

5. The flow cytometry apparatus of claim 4, wherein the micro-flow device comprises a microfluidic chip.

6. The flow cytometry apparatus of claim 2, wherein the waste receptacle is positioned downstream from the droplet generator, and wherein the first collection vessel and the second collection vessel are positioned downstream from the waste receptacle.

7. The flow cytometry apparatus of claim 1, wherein:
the first momentum is produced by forming said first interference droplets with a first property selected from the group consisting of: mass and velocity; and
the second momentum is produced by forming said second interference droplets with a second property selected from the group consisting of: mass and velocity.

8. The flow cytometry apparatus of claim 1, wherein the source flow is a laminar flow.

9. The flow cytometry apparatus of claim 1, wherein the source flow is surrounded by a gas.

10. The flow cytometry apparatus of claim 1, wherein the source flow is separated into a stream of sample droplets.

11. The flow cytometry apparatus of claim 1, wherein the droplet generator comprises a piezoelectric print head.

12. The flow cytometry apparatus of claim 1, wherein the droplet generator comprises a flow cytometry droplet generator nozzle.

13. The flow cytometry apparatus of claim 1, wherein the droplet generator produces interference droplets asynchronously.

14. The flow cytometry apparatus of claim 1, wherein the interference droplets and the source flow comprise the same fluid.

* * * * *